United States Patent [19]

O'Dell

[11] Patent Number: 5,356,771
[45] Date of Patent: Oct. 18, 1994

[54] COMBINED PERFUSION AND OXYGENATION ORGAN PRESERVATION APPARATUS

[75] Inventor: Bobby J. O'Dell, San Antonio, Tex.

[73] Assignee: Board of Regents, The University of Texas System, Austin, Tex.

[21] Appl. No.: 29,881

[22] Filed: Mar. 11, 1993

[51] Int. Cl.$^5$ .............................................. A01N 1/02
[52] U.S. Cl. ...................................... 435/1; 435/283; 435/289; 261/35; 261/122.1
[58] Field of Search ................... 435/1, 283, 284, 287, 435/289; 422/1; 62/372; 137/67, 206, 576; 261/35, 122.1

[56] References Cited

U.S. PATENT DOCUMENTS

| | | | |
|---|---|---|---|
| 3,632,473 | 1/1972 | Belzer et al. | 435/1 |
| 3,777,507 | 12/1973 | Burton et al. | 435/283 X |
| 3,818,934 | 6/1974 | Borsanyi | 435/283 X |
| 3,843,455 | 10/1974 | Bier | 435/283 X |
| 3,892,628 | 7/1975 | Thorne et al. | 435/283 X |
| 3,914,954 | 10/1975 | Doerig | 435/1 X |
| 3,935,065 | 1/1976 | Doerig | 435/1 |
| 4,186,565 | 2/1980 | Toledo-Pereyra | 435/1 X |
| 4,242,883 | 1/1981 | Toledo-Pereyra | 435/1 X |
| 4,745,759 | 5/1988 | Bauer et al. | 435/1 X |
| 4,837,390 | 6/1989 | Reneau | 435/283 X |
| 4,951,482 | 8/1990 | Gilbert | 62/457.1 |
| 5,051,352 | 9/1991 | Martindale et al. | 435/1 |
| 5,141,847 | 8/1992 | Sugimachi et al. | 435/1 |
| 5,217,860 | 6/1993 | Fahy et al. | 435/1 |

OTHER PUBLICATIONS

M. Yland, et al., "A Homeostatic Perfusion Method and Apparatus: A New Approach to In Vitro Hibernation," manuscript, Depts. of Surgery and Anesthesiology, University Hospital Stony Brook, Stony Brook, N.Y. (undated).
Petsika, et al., "Adenosine Enhances Left Ventricular Flow During 24-Hour Hypothermic Perfusion of Isolated Cardiac Allografts," 9 J. Heart Transpl. pp. 543–547 (1990).
Minten, et al., "Differences in High-Energy Phosphate Catabolism Between the Rat and the Dog in a Heart Preservation Model," 10 J. Heart and Lung Transpl. pp. 71–78 (1991).
Wicomb, et al., "Value of Polyethylene Glycol (PEG) and Horseradish Peroxidase (HRP) for Hypothermic Rabbit Heart Perfusion," 21 Transpl. Proc. pp. 1366–1368 (1989).
Qayumi, et al., "Comparison of Functional and Metabolic Assessments in Preservation Techniques for Heart Transplantation," 4 J. Investigative Surgery pp. 93–102 (1991).

Primary Examiner—Jeffrey R. Snay
Attorney, Agent, or Firm—Arnold, White & Durkee

[57] ABSTRACT

A method and apparatus is provided for long-term extracorporeal preservation of living tissue. A tissue preservation device including a gas permeable membrane and perfusate allows oxygenation of the living tissue. The gas permeable membrane allows gas from a cyclically pumped source to permeate and expand the membrane, simultaneously oxygenating the perfusate and pumping the oxygen-enriched perfusate through the tissue. Simply constructed of a few basic components, the tissue preservation device is capable of operating in many physical orientations, and requires no electrical power for operation. Also provided is an apparatus for cooling and transporting the tissue preservation device.

12 Claims, 2 Drawing Sheets

COMBINED PERFUSION AND OXYGENATION ORGAN PRESERVATION APPARATUS

BACKGROUND OF THE INVENTION

The present invention relates to an apparatus and method for highly portable perfusion for long-term extracorporeal preservation of living tissue.

Although tissue transplantation and implantation have been viable since the 1960's, and have increased in popularity since that time, techniques for preservation of tissue have not become normalized. Initially, simple cold storage was used. Perfused cold storage and hyperbaric cold perfused storage were subsequently shown experimentally to be superior to simple unperfused cold storage. Since both techniques could not be practically applied, nonperfused cold storage continued to be preferred. A disadvantage of simple nonperfused cold storage, however, is the limited period of viability of the tissue, typically due to significant oxygen loss.

Because of the distance that often separates tissue donors and recipients, the portability of storage devices is of critical importance. In addition, the desire to increase the pool of tissue available for transplantation into any one recipient mandates that the storage time for the tissue be extended beyond that permitted with simple hypothermic storage, thus opening the possibility for a world-wide network of donors and recipients.

Pulsatile perfusion devices have been developed to sustain and extend the viability of extracorporeal living tissue for several hours pending the implant of the tissue. The advantage of this technique is that it mimics the natural state of the tissue by inducing flow through its arterial supply of oxygenated fluid, or perfusate. However, only limited success has been achieved with perfusion of tissue in the atmosphere (i.e., without submersing the perfused tissue in the perfusate). The danger of this method of perfusion is that a pressure gradient may develop across the capillary wall of the tissue, which is proportionate to the output of the perfusion pump. Under hypothermic conditions, perfusion pressures in excess of 20 mm Hg have resulted in capillary damage destroying and compromising the viability of the tissue being preserved.

Hypothermic perfusion of tissue during storage can significantly extend storage time to 12-24 hours, without loss of tissue viability, due to reduced tissue metabolic rate and oxygen consumption. For example, cooling to 15° C., in the presence of oxygen, reduces oxygen consumption of myocardial tissue to one-fifth of the rate at normal body temperature. However, hypothermia alone is less protective than when it is combined with oxygenated perfusion, in that a continuous supply of oxygen is available in the latter case to support the remaining metabolic oxygen requirements.

Hypothermic perfusion devices have been designed and are known in the art. However, devices that are currently available for hypothermic perfusion are large, require significant volumes of compressed gas and electrical power, and/or also may necessitate an upright level orientation for operation.

One such device is that contemplated by Doerig, U.S. Pat. No. 3,914,954. Doerig appears to disclose an organ perfusion device that, in one embodiment, submerges the organ being preserved in the perfusate and pumps perfusate through the organ. The perfusate is oxygenated through a separate gas inlet valve. No provision is made, however, for sealing the perfusate from the lid of the device, thus leaving the perfusate open to atmospheric pressure, permitting the level of the perfusate to fluctuate, and also providing a means by which biological or chemical contaminants can enter the system. Like most conventional perfusing units, the Doerig device is significantly limited in its portability due to the necessity of maintaining the device in an upright orientation. Travel over extended distances, as is becoming increasingly necessary in modern times, would increase the likelihood of upsetting this delicate balance and endangering the organ.

SUMMARY OF THE INVENTION

The problems outlined above are addressed by the apparatus and method of the present invention. That is, the invention makes it possible to produce a completely portable extracorporeal living tissue preservation device that is independent of electricity and is adjustable to operation in any physical orientation, yet includes pumping, oxygenating and chilling characteristics that can maintain the oxygenation and perfusion of living tissue for up to 24 hours or more.

Broadly speaking, the present invention contemplates a method and apparatus for hypothermic perfusion and oxygenation of extracorporeal living tissue. The apparatus includes a living tissue preservation device, which comprises two chambers. A tissue chamber comprises a tissue compartment capable of receiving perfusate and living tissue. A gas permeable membrane sealingly divides the tissue compartment from a cavity created at the top of the chamber. A pumping chamber comprises a perfusing compartment, which is capable of receiving perfusate. A gas permeable membrane sealingly divides the perfusate in the pumping chamber from a pumping compartment, which is formed in a cavity between the membrane and the top of the chamber. The pumping chamber is connected to the tissue chamber by an inlet and an outlet port, each comprised of tubing and one-way valves.

A pumping device, such as a pressure controlled ventilator, is coupled to the pumping compartment, and is connectable to gas compression cylinders to cyclically force any properly proportioned oxygen-containing gas, such as 100% oxygen or a combination of oxygen and carbon dioxide, etc., into the pumping compartment, where the gas is diffused through the membrane into the perfusing compartment. Oxygen-enriched perfusate from the perfusing compartment is then transmitted through a one-way valve into the tissue in the tissue compartment. Because the tissue is submerged in perfusate in a hermetically sealed container, each flow pulse during perfusion results in a rise in pressure in both the capillaries as well as in the storage container. The result is that extremely small pressure gradients are generated across the capillary wall, potentially reducing damage and minimizing edema formation in the tissue being preserved. The device of the present invention can also perfuse while the compartments are under an elevated pressure. This hyperbaric perfusion enhances oxygenation, and combined with the cool temperature further conserves the oxygenated gas supply.

The preferred configuration of the two chambers is a side-by-side arrangement (shown in FIG. 1), which allows convenient access to the organ in the organ chamber and achieves an optimal balance between operating power and pump head pressure. Additionally, this configuration is stable and resists tipping. Alternatively, if desired due to space concerns or other reasons, the chambers may be stacked one on top of the other. It has been found that having the organ chamber on top allows convenient access to the organ and also facilitates ease of access; further, the pump head pressure in this configuration allows for high perfusate flow. One disadvantage of this configuration, however, is the increased use of oxygen. Having the pumping chamber on top requires less power to operate and is best for low-flow use (i.e., pump head pressure is reduced), but renders access to the organ chamber less convenient. The amount of perfusate required remains the same for all three configurations.

The present invention also contemplates a method of perfusing extracorporeal living tissue, which includes attaching the arterial supply (if any) of the living tissue to a tube adaptor and placing the connected tissue into the perfusate-filled tissue compartment of the device. The tube adapter is then connected to the inlet port to allow perfusate flow from the perfusing compartment into the tissue in the tissue compartment. Oxygenation of the perfusate and tissue is then accomplished by supplying compressed, properly proportioned, oxygen-containing gas to the pumping compartment, injecting the gas at regular intervals into the pumping compartment, and pressurizing the gas side of the membrane. Gas permeates the membrane and oxygenates the perfusate in the perfusing compartment. Simultaneously, the pressure difference between the pumping and perfusing compartments results in an expansion of the membrane into the perfusing compartment to allow the oxygenated perfusate to enter the tissue through a one-way inlet port valve. During the perfusing cycle, pressure builds up in the tissue compartment. This pressure is equalized by the membrane and the weight of the perfusate reserve, or may be equalized by other known methods of compliance. After the pressure cycle, the one-way valve in the outlet port opens, allowing the pressure to equalize between the two compartments. This action allows fluid from the tissue compartment to flow through the outlet port to the perfusing compartment where the gas, now primarily comprising carbon dioxide, is permeated through the membrane and removed from the pumping compartment by the exhaust valve. The cycle is repeated at the next gas injection interval.

An important feature of the present invention is the central role of the gas permeable membranes. In the preferred method of operation, the membrane in the pumping chamber performs multiple functions, including pumping perfusate from the perfusing compartment into the tissue compartment and allowing the exchange of gases in the perfusing compartment. Additionally, the membrane provides a seal between the perfusate and the pumping compartment. The membrane in the tissue chamber allows equalization of pressure built up during the perfusing cycle (compliance), and also allows excess gas to diffuse the membrane and escape through a vent in the tissue chamber. Alternatively, a tightly sealed, flexible chamber with other venting or compliance configurations will obviate the need for a membrane in the tissue chamber.

Because the perfusate is tightly sealed within the perfusing and tissue compartments, the device is capable of operating during substantial physical reorientation. Thus, brief tipping of the chambers will not impair the operation of the device; however, adjustments to gas input pressure must be made to continue operation if the orientation of the device is significantly altered.

As noted earlier, hypothermia of the tissue and perfusate may extend the viability of the tissue. A preferred storage temperature is 4° C.±1° C., which may be attained by placing the device(s) into a cold storage unit, such as a sturdy, insulated ice chest packed with cold packs.

The present invention therefore provides an improved apparatus and method that allow convenient and relatively long-term storage and transportation of living tissue. The perfusion device of the invention is relatively simple in design, and the dual-chamber design has the advantage of flexibility in the selection of varying sized tissue compartments to accommodate large or small tissue volumes. Portability of living tissue is enhanced by the device's electricity-free operation and adjustability to physical reorientation.

It is important to note that the present invention comprises only an apparatus and method for more conveniently and consistently perfusing and oxygenating tissue at a rate and pressure which others have used with success. Actual preservation of living tissue will require the knowledge of experts in the field of tissue harvesting and transplantation. Accordingly, the details for actual preservation of living tissue are neither claimed nor attempted to be disclosed herein.

The ability of the present invention to conveniently and consistently perfuse living tissue for longer periods than currently available in the art may increase tissue viability, which would have the following benefits:

1. The geographical area from which tissue could be obtained would be increased, thereby increasing tissue availability;
2. The increased tissue availability would increase the quality of tissue cross-matching, thus reducing rejection;
3. With longer tissue viability periods, tissue transplantation may potentially be moved from a high priority emergency procedure to possibly a scheduled procedure; and
4. Since donor tissue would be in better condition after storage according to the present invention, transplantation success rates should improve.

The advantages of the present invention will be further appreciated from the drawings and from the detailed description provided below.

BRIEF DESCRIPTION OF THE DRAWINGS

The herein described advantages and features of the present invention, as well as others which will become apparent, are attained and can be understood in more detail by reference to the following description and appended drawings, which form a part of this specification.

It is to be noted, however, that the appended drawings illustrate only exemplary embodiments of the invention and are therefore not to be considered limiting of its scope, for the invention may admit to other equally effective embodiments.

DETAILED DESCRIPTION OF THE PREFERRED EMBODIMENTS

Figure 1:
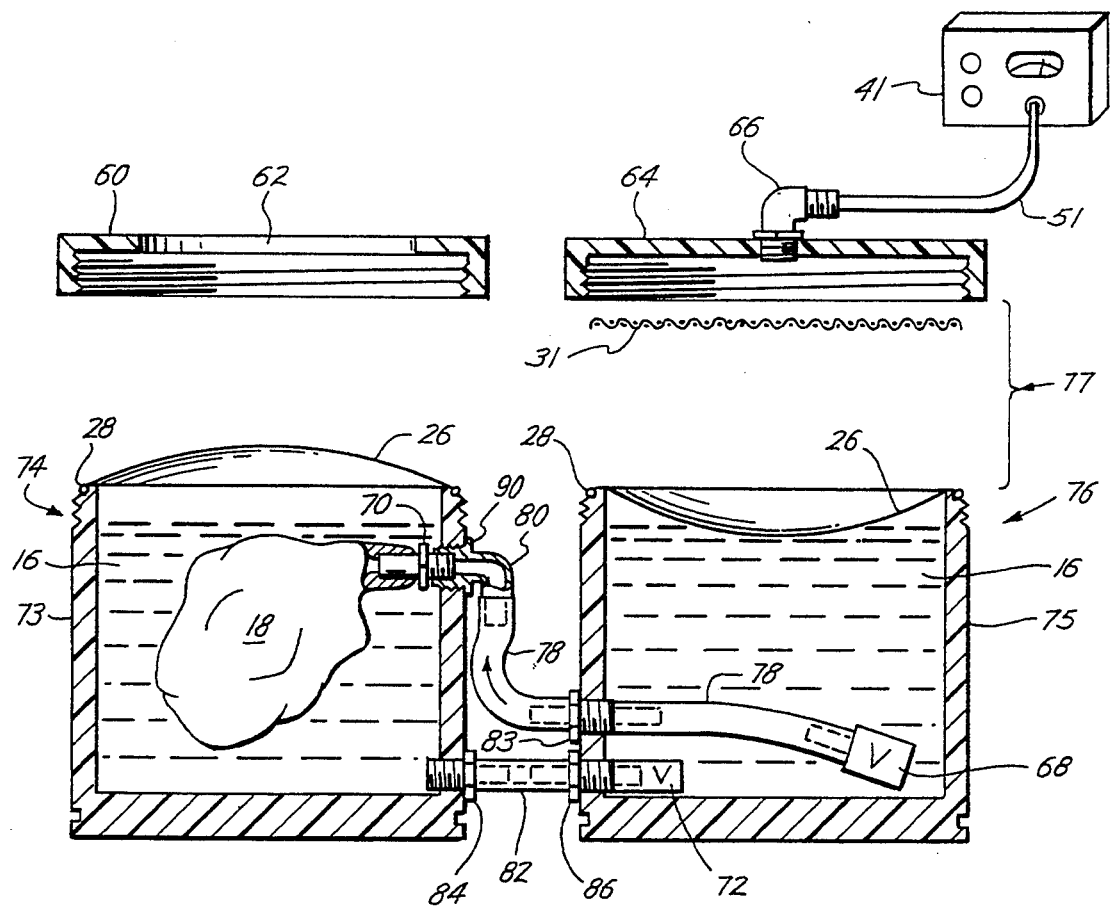
FIG. 1 is a cross-section, exploded view of perfusion apparatus according to the present invention.
Figure 2:
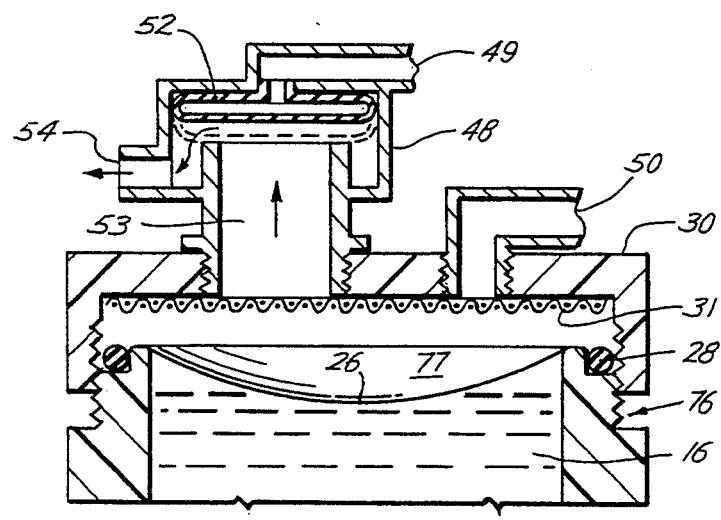
FIG. 2 is a cross-section view of a gas inlet/outlet device that may be used in accordance with the present invention.

Turning now to the drawings, FIG. 1 is a cross-section exploded view of a perfusion device according to the present invention. Tissue chamber 74 comprises tissue compartment 73, which is capable of receiving perfusate 16 and living tissue 18. In the preferred method of operation, tissue compartment 73 is filled with perfusate 16. The arterial supply, if any, of tissue 18 is connected to tube adapter 70. Tissue 18 is then inserted into the perfusate-filled tissue compartment 73, and tube adapter 70 is, for stability, preferably connected to securing bracket 90 affixed to a wall of tissue chamber 74. Tissue compartment 73 is sealed with gas permeable membrane 26. To secure membrane 26 tightly within tissue chamber 74, an o-ring constructed of, for example, flexible tubing 28 (such as Silastic TM brand tubing manufactured by Dow Corning) is placed over membrane 26 to create a snug fit when lid 60 is attached to tissue chamber 74. Alternatively, membrane 26 may be placed over flexible tubing 28 to achieve the same effect, as shown in FIG. 2. Although lid 60 is shown threaded for attachment to tissue compartment 73, other methods of creating a tight, hermetically sealed fit such as latches, snap-on lids, etc., are acceptable. Lid opening 62 allows excess gas to escape tissue chamber 74. To prevent membrane 26 from being trapped against the lid opening 62, screen 31 may be placed between membrane 26 and lid 60. Tissue chamber 74 may alternatively be comprised of a flexible, tightly sealable container, removing one need for flexible gas permeable membrane 26 in tissue chamber 74. Other suitable means for providing compliance in the tissue chamber will be apparent to those skilled in the art.

Pumping chamber 76 is comprised of perfusing compartment 75 and pumping compartment 77. Perfusing compartment 75 is capable of receiving perfusate 16, and is sealingly divided from pumping compartment 77 by gas permeable membrane 26. Pumping compartment 77 is a cavity created between membrane 26 and lid 64. An o-ring constructed of, for example, flexible tubing 28 is preferably placed over membrane 26 to create a snug fit when lid 64 is attached to perfusing compartment 75. Alternatively, membrane 26 may be placed over flexible tubing 28 to achieve the same effect, as shown in FIG. 2. Although lid 64 is shown threaded for attachment to perfusing compartment 75, other methods of creating a tight, hermetically sealed fit such as latches, snap-on lids, etc., are acceptable, as noted above.

Pumping chamber 76 is connectable to tissue chamber 74 by inlet tubing 78 and outlet tubing 82. Bracket holders 90 and 83 secure inlet tubing 78 between tissue compartment 73 and perfusing compartment 75; similarly, bracket holders 84 and 86 secure outlet tubing 82 between tissue compartment 73 and perfusing compartment 75. During oxygenation, pumping device 41 pumps gas through connective tubing 51 into, for example, two-way connector 66 and into pumping compartment 77. A suitable pumping device 41 may be, for example, a Mark 7 or Mark 14 model pressure controlled ventilator manufactured by Bird Corporation, or a Healthdyne Impulse Ventilator Model 303. The exhaust valve illustrated FIG. 2 is also compatible with the perfusion device illustrated in FIG. 1, with lid 30 substituted for lid 64. Alternatively, other gas inlet-outlet devices that provide for cyclical input of a properly proportioned gas and for expulsion of gas are also acceptable.

During the gas input cycle, the increased concentration of oxygen in pumping compartment 77 creates a negative pressure in perfusing compartment 75, which causes gas to permeate membrane 26 and oxygenate perfusate 16 in perfusing compartment 75. Simultaneously, the difference in pressure expands membrane 26 and forces oxygenated perfusate 16 from perfusing compartment 25 through one-way inlet valve 68 and through inlet tubing 78 and into living tissue 18. During the off cycle of the pumping device, one-way outlet valve 72 will open due to the relatively negative pressure created in perfusing compartment 68, and allow gas-enriched perfusate to flow from tissue compartment 73 through outlet tubing 82 and into perfusing compartment 68. The low carbon dioxide concentration in pumping compartment 77 will induce the gas, now consisting primarily of carbon dioxide released from tissue 18, to permeate membrane 26 into pumping compartment 77, where it is expelled through two-way valve 66.

Membrane 26 need not necessarily be elastic, but must be sufficiently flexible to allow the surface of the membrane to follow the surface of the perfusate. Further, membrane 26 must be permeable. An exemplary gas permeable membrane 26 contemplated by the present invention has the following properties:

Oxygen permeability at 4° C.: 3,500 ml $O_2$/min/$m^2$
$CO_2$ permeability at 4° C.: 21,000 ml $CO_2$/min/$m^2$
Membrane thickness: 0.09 mm maximum
Porosity: Membrane porosity should be sufficient to prevent diffusion of water in its liquid phase.
Elasticity: Minimum elongation at break 30%; minimum burst strength 10 psi.

Suitable materials include silicone rubber, polydimethylsiloxane (PDMS), polytetrafluoroethylene (PTFE), dimethyl and methyvinyl siloxane copolymers both unsupported and supported on polyester, or like fibers. Commercially available membranes meeting these specifications include the True Membrane TM manufactured by Avcore Inc. of Plymouth, Minn., the Silon TM membrane manufactured by Bio Med Sciences, Inc. of Pennsylvania, and the Silastic TM membrane manufactured by Dow Corning of Midland, Mich.

A suitable perfusate 16 for use with the device and method of the present invention is the University of Wisconsin Solution with HES or PEG, as referenced in Wicomb et al., 48 *Transplantation* 6–9 (1989) and 49 *Transplantation* 261–64 (1990), the disclosures of which are expressly incorporated herein by reference. Other general categories of acceptable perfusion/storage media compatible with the present invention include the perfusion/storage media described in the following references, disclosures of which are each expressly incorporated herein by reference:

1. Modified Krebs-Henseleit Solution, as referenced in Petsikas et al., 9 *J. Heart Transplantation* 543–547 (1990).
2. Bretschneider HTK Solution, as referenced in Minten et al., 10 *J. Heart and Lung Transplantation* 71–78 (1991).
3. Wicomb Solution, as referenced in Wicomb et al., 21 *Transplantation Proceedings* 1366–68 (1989).
4. Tyers' Solution, as referenced in Qayumi et al., 4 *J. Investigative Surgery* 93–102 (1991).

In an alternative configuration, lids 62 and 64 may switched so that the incoming gas is pumped through membrane 26 and into tissue compartment 73. In this reverse configuration, the oxygenated perfusate will be pumped into perfusion compartment 76 through valve 72 during the pump cycle, and will be drawn back through valve 68 into organ 18 during the off cycle. This configuration may have advantages in that the oxygenated perfusate is drawn into the organ, rather than pumped through it. A disadvantage of this configuration, however, is that access to the organ is reduced.

FIG. 2 illustrates a suitable gas inlet/outlet device for use with the perfusion apparatus of the present invention. Lid 30 would replace lid 64 depicted in FIG. 1. This device comprises gas inlet valve 50 and gas exhaust valve 48. Properly proportioned, oxygen-containing gas is pumped from a pressure-controlled ventilator (see FIG. 1) into gas inlet valve 50 and also through gas input port 49 into exhaust valve 48. During gas input, bladder 52 in the exhaust valve expands from the pressure of the incoming gas to seal exhaust channel 53. Simultaneously, gas pumped into gas inlet valve 50 enters pumping compartment 77. During the off cycle of the pressure controlled ventilator, bladder 52 in gas exhaust valve 48 is relaxed, as shown in FIG. 2, allowing gas to be exchanged in the pumping compartment 77, and released through exhaust channel 53 and out gas exhaust port 54. An exhaust valve 48 that performs as described above is an expiratory valve manufactured by Bird Corporation, model number 999-2576.

Clinical trials of prototypes of the claimed tissue preservation apparatus and cold storage unit on canine hearts have successfully perfused and chilled the organs for at least 12 hours. In contrast, it has been determined that the partial pressure of oxygen in the tissue will decline rapidly after 5 hours in simple hypothermic storage (such as storage of the tissue in a container packed in ice).

The present invention is not limited to preserving myocardia; any living tissue in which the main arterial supply vessel can be isolated and cannulated can potentially be stored in the claimed device. This includes organs such as lungs, kidneys, livers, and pancreas, and extremities such as fingers and toes. In addition, tissue (e.g., corneas) that cannot be perfused but requires precise hypothermic storage can also be maintained within the claimed device.

Figure 3:
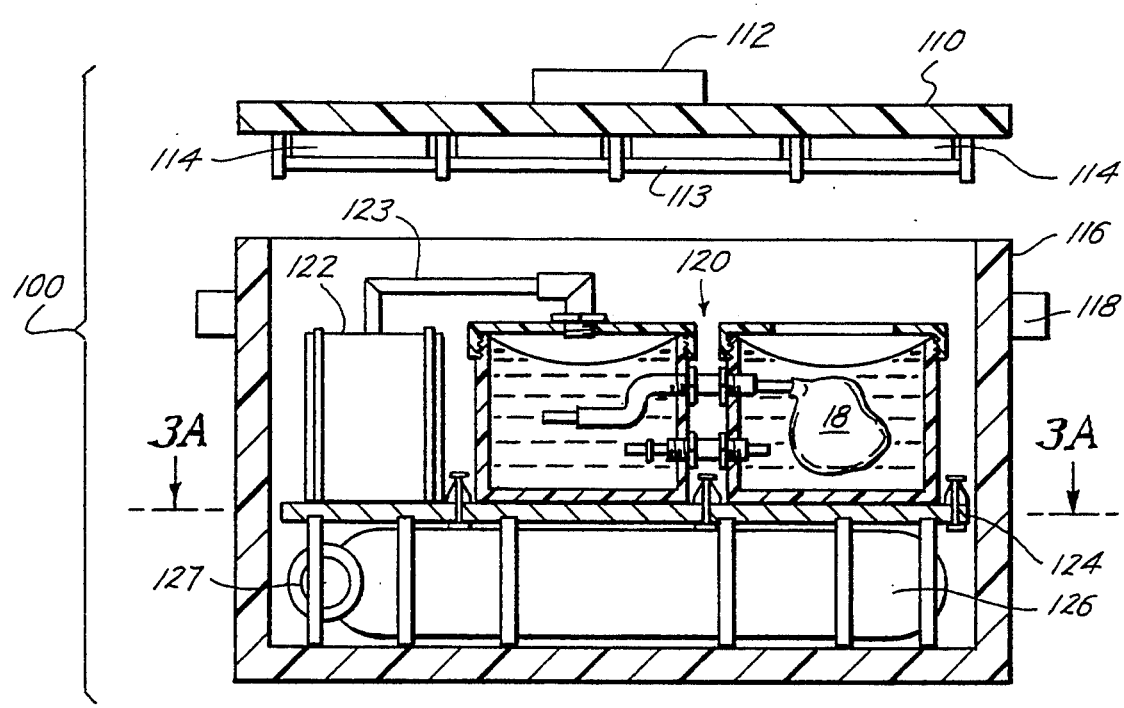
FIG. 3 is a cross-section, exploded view of apparatus suitable for cooling and transporting the perfusion apparatus of the present invention.

FIG. 3 illustrates a cooling and transportation apparatus that is suitable for the perfusion apparatus of the present invention. Cooling and transportation unit 100 is preferably insulated and lightweight, yet sturdy. Many conventional ice chests will be suitable for this purpose. As shown in FIG. 3, cooling unit 100 has removable lid 110 with lid handle 112 and side handles 118. Integrated into lid 110 is cooling tray 113, which holds a cooling means such as ice, ice packs, or cold packs. Illustrated in FIG. 3 are cold packs 114, which may be X-Coldbrick TM cold packs, manufactured under model number XC24BR by Pelton Shepherd Industries of California. Approximately two cold packs per 500 cc's of perfusate solution can maintain the tissue and solution at 4° C.±1° C. for as long as 24 hours.

Careful use of the cold packs is required to avoid damaging the tissue by overchilling. For example, it is undesirable to place the cold packs in close proximity with the perfusion apparatus 120; otherwise, cold spots in the perfusate may result. Therefore, cooling tray 113 is placed above perfusion apparatus 120 so as to allow air circulation. Cooling tray 113 is preferably perforated or otherwise configured to allow air circulation around the cooling means.

Figure 3A:
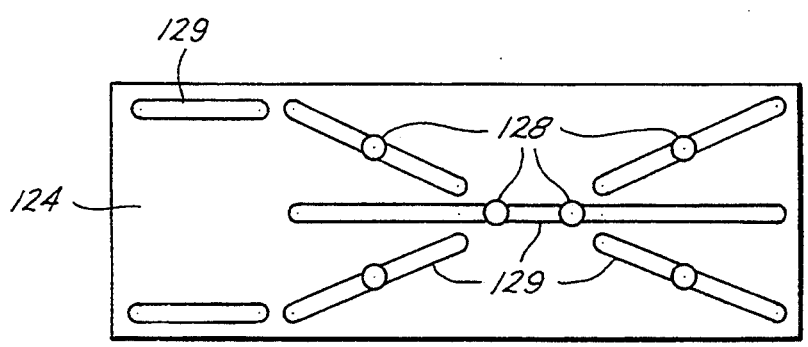
FIG. 3A is a cross-section view along section 3A—3A of FIG. 3.

Illustrated in FIG. 3A is supporting shelf 124, which separates perfusion apparatus 120 and pump 122 from one or more oxygen cylinders 126. A preferred configuration includes two size "D" oxygen cylinders. Integrated into supporting shelf 124 are slots 129, which allow air circulation. Slot-adjustable stabilizing clips 128 are used to hold perfusion apparatus 120 and pump 122 into place and prevent shifting during transportation.

Perfusion apparatus 120 is shown in FIG. 3 connected to pump 122 by tubing 123. In turn, pump 120 (which may be a Mark 7 Bird Respirator, for example) is coupled to oxygen cylinder 126 through valve 127.

Using conventional ice chests, a suitable cooling and storage apparatus may be constructed in accordance with the present disclosure that will provide a convenient, yet lightweight (approximately 50 lbs) means for transporting and cooling the perfusion apparatus of the present invention.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. An apparatus for perfusing and oxygenating living tissue, comprising:

a pumping compartment;

a perfusion compartment coupled to said pumping compartment and containing a perfusate;

a tissue compartment coupled to said perfusion compartment and containing a perfusate and adapted to receive a living tissue;

a first one-way passage means coupling said perfusion compartment and said tissue compartment for transmitting perfusate from said perfusion compartment to a living tissue in said tissue compartment;

a second one-way passage means coupling said perfusion compartment and said tissue compartment for transmitting perfusate from said tissue compartment to said perfusion compartment;

a flexible, gas-permeable membrane sealingly interposed between said pumping compartment and said perfusate within said perfusion compartment for enabling gas to permeate between said pumping compartment and said perfusion compartment, said membrane operable upon pressure differentials across the membrane to flex in a first direction so as to displace perfusate through said first passage means from said perfusion compartment into said tissue compartment and in an opposite direction to displace perfusate from said tissue compartment through said second passage means into said perfusion compartment; and gas circulation means coupled to said pumping compartment for forcing an oxygen-containing gas into said pumping compartment to permeate the oxygen-containing gas through said membrane into said perfusing compartment and to expand said membrane into said perfusing compartment so as to pump gas-enriched perfusate from said perfusing compartment through said first one-way passage means into said tissue compartment.

2. The apparatus as recited in claim 1, wherein said circulation means comprises:

a two-way inlet/outlet valve coupled to said pumping compartment for delivering a gas into and out of said pumping compartment.

3. The apparatus as recited in claim 1, wherein said circulation means comprises:

an inlet valve coupled to said pumping compartment for delivering said oxygen-containing gas into said pumping compartment; and an exhaust valve coupled to said pumping compartment for exhausting gas out of said pumping compartment.

4. The apparatus as recited in claim 1, wherein said tissue compartment comprises at least one wall capable of flexing in response to entry and exit of said perfusate.

5. The apparatus of claim 1, wherein said perfusate comprises a liquid capable of dissolving oxygen and carbon dioxide.

6. The apparatus of claim 5, wherein said gas-permeable membrane is substantially impermeable to said perfusate.

7. An apparatus for perfusing and oxygenating living tissue, comprising:

a pumping compartment including a two-way connection for enabling flow of gas to or from said pumping compartment;

a perfusion compartment coupled to said pumping compartment and capable of containing perfusate;

a tissue compartment capable of containing a living tissue and perfusate;

a first one-way passage means coupling said perfusion compartment and said tissue compartment and connectable to a living tissue for transmitting perfusate from said perfusion compartment to said living tissue in said tissue compartment;

a second one-way passage means coupling said perfusion compartment and said tissue compartment for transmitting perfusate from said tissue compartment to said perfusion compartment; and a flexible, gas-permeable membrane sealingly interposed between said pumping compartment and said perfusion compartment for enabling gas to permeate between said pumping compartment and said perfusion compartment, said membrane operable upon pressure differentials across the membrane to flex in a first direction so as to displace perfusate from said perfusion compartment through said first passage means into said tissue compartment and in an opposite direction so as to displace perfusate from the tissue compartment through said second passage means into said perfusion compartment.

8. The apparatus recited in claim 7, further comprising gas circulation means coupled to said pumping compartment for forcing an oxygen-containing gas into said pumping compartment and causing permeation of the gas through said membrane and for flexing said membrane into said perfusion compartment to pump perfusate through said living tissue.

9. An apparatus for perfusing and oxygenating living tissue, comprising:

a pumping compartment including a connection for directing a flow of oxygen-containing gas to or from said pumping compartment;

a perfusion compartment adapted to contain perfusate;

a tissue compartment coupled to said pumping compartment and adapted to receive a living tissue and perfusate;

a first passage means coupling said perfusion compartment and said tissue compartment for selectively transmitting a gas-enriched perfusate from said tissue compartment to said perfusion compartment;

a second passage means coupling said perfusion compartment and said tissue compartment for selectively transmitting a gas-enriched perfusate from said perfusion compartment to a living tissue in said tissue compartment; and a flexible, gas-permeable membrane means sealingly interposed between said pumping compartment and said tissue compartment for enabling gas to permeate from said pumping compartment through said membrane means to said tissue compartment, said membrane operable upon opposing pressure differentials across the membrane to flex in a first direction so as to displace perfusate from said tissue compartment through said first passage means into said perfusion compartment and in an opposite direction to displace gas from the tissue compartment through said membrane and to displace perfusate from said perfusion compartment through said second passage means and into said tissue.

10. Apparatus for perfusing living tissue, comprising:

a tissue chamber having a top opening and capable of containing living tissue and perfusate;

a first flexible, gas-permeable membrane sealing the top opening of the tissue chamber;

a perfusate chamber having a top opening and capable of holding perfusate;

a second flexible, gas-permeable membrane sealing the top opening of the perfusate chamber;

a first closure device capable of closing either of said sealed chambers and defining a first cavity between said first closure device and the membrane sealing the chamber closed by the first closure device, said first closure device including a two-way flow device enabling a flow of gas selectively to or from said cavity;

a second closure device capable of closing either of said sealing chambers and defining a second cavity between said second closure device and the membrane sealing the chamber closed by the second closure device, said second closure device including a vent connection for venting said second cavity;

a first one-way passageway interconnecting said chambers and enabling fluid to flow from said perfusate chamber to said tissue in the tissue chamber; and a second one-way passageway interconnecting said chambers and enabling fluid to flow from said tissue chamber to said perfusate chamber.

11. The apparatus of claim 10, wherein the first closure device closes the perfusate chamber.

12. The apparatus of claim 10, wherein the first closure device closes the tissue chamber.

* * * * *